(12) United States Patent
Wang et al.

(10) Patent No.: US 9,983,571 B2
(45) Date of Patent: *May 29, 2018

(54) TELE-PRESENCE ROBOT SYSTEM WITH SOFTWARE MODULARITY, PROJECTOR AND LASER POINTER

(71) Applicant: INTOUCH TECHNOLOGIES, INC., Goleta, CA (US)

(72) Inventors: Yulun Wang, Goleta, CA (US); Marco Pinter, Goleta, CA (US); Kevin Hanrahan, Santa Barbara, CA (US); Daniel Steven Sanchez, Summerland, CA (US); Charles S. Jordan, Mill Spring, NC (US); David Bjorn Roe, Santa Barbara, CA (US); James Rosenthal, Santa Barbara, CA (US); Derek Walters, Campbell, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/518,978

(22) Filed: Oct. 20, 2014

(65) Prior Publication Data

US 2015/0038983 A1 Feb. 5, 2015

Related U.S. Application Data

(62) Division of application No. 12/425,835, filed on Apr. 17, 2009, now Pat. No. 8,897,920.

(51) Int. Cl.
*G05B 19/414* (2006.01)
*B25J 5/00* (2006.01)
(Continued)

(52) U.S. Cl.
CPC ............ *G05B 19/414* (2013.01); *A61B 34/30* (2016.02); *A61B 34/35* (2016.02); *A61B 34/37* (2016.02);
(Continued)

(58) Field of Classification Search
CPC ... B25J 5/00; B25J 9/162; B25J 9/1689; B25J 9/1697; B25J 9/161; B25J 19/022;
(Continued)

(56) References Cited

U.S. PATENT DOCUMENTS

| 4,107,689 A | 8/1978 | Jellinek |
| 4,213,182 A | 7/1980 | Eichelberger et al. |

(Continued)

FOREIGN PATENT DOCUMENTS

| CN | 1404695 A | 3/2003 |
| CN | 1561923 A | 1/2005 |

(Continued)

OTHER PUBLICATIONS

"Nomad Scout User's Manual", Nomadic Technologies, Software Version 2. 7, Part No. DOC00004, Jul. 12, 1999, pp. 1-59.

(Continued)

*Primary Examiner* — Stephen Holwerda

(57) ABSTRACT

A remote control station that accesses one of at least two different robots that each have at least one unique robot feature. The remote control station receives information that identifies the robot feature of the accessed robot. The remote station displays a display user interface that includes at least one field that corresponds to the robot feature of the accessed robot. The robot may have a laser pointer and/or a projector.

4 Claims, 16 Drawing Sheets

(51) Int. Cl.
*B25J 9/16* (2006.01)
*B25J 19/02* (2006.01)
*A61B 90/00* (2016.01)
*A61B 34/30* (2016.01)
*A61B 34/37* (2016.01)
*A61B 34/35* (2016.01)

(52) U.S. Cl.
CPC ............... *A61B 90/361* (2016.02); *B25J 5/00* (2013.01); *B25J 9/161* (2013.01); *B25J 9/162* (2013.01); *B25J 9/1689* (2013.01); *B25J 9/1697* (2013.01); *B25J 19/022* (2013.01); *Y10S 901/01* (2013.01)

(58) Field of Classification Search
CPC ............ A61B 19/5212; A61B 19/2203; A61B 2019/2223; A61B 2019/223; G05B 19/414; Y10S 901/01
USPC ..... 348/14.01, 14.03, 14.05, 14.08; 700/245, 700/248, 259
See application file for complete search history.

(56) References Cited

U.S. PATENT DOCUMENTS

| | | | |
|---|---|---|---|
| 4,553,309 A | | 11/1985 | Hess et al. |
| 4,697,278 A | | 9/1987 | Fleischer |
| 5,617,539 A | | 4/1997 | Ludwig et al. |
| 5,673,082 A | * | 9/1997 | Wells ..................... G01S 7/493 348/139 |
| 5,793,365 A | | 8/1998 | Tang et al. |
| 5,867,494 A | | 2/1999 | Krishnaswamy et al. |
| 6,091,219 A | | 7/2000 | Maruo et al. |
| 6,292,714 B1 | | 9/2001 | Okabayashi |
| 6,314,631 B1 | | 11/2001 | Pryor |
| 6,317,953 B1 | | 11/2001 | Pryor |
| 6,373,855 B1 | | 4/2002 | Downing et al. |
| 6,411,055 B1 | | 6/2002 | Fujita et al. |
| 6,567,038 B1 | | 5/2003 | Granot et al. |
| 6,667,592 B2 | | 12/2003 | Jacobs et al. |
| 6,674,259 B1 | | 1/2004 | Norman et al. |
| 6,693,585 B1 | | 2/2004 | MacLeod |
| 6,816,754 B2 | | 11/2004 | Mukai et al. |
| 6,893,267 B1 | | 5/2005 | Yueh |
| 6,990,112 B1 | | 1/2006 | Brent et al. |
| 7,011,538 B2 | | 3/2006 | Chang |
| 7,053,578 B2 | | 5/2006 | Diehl et al. |
| 7,055,210 B2 | | 6/2006 | Keppler et al. |
| 7,222,000 B2 | | 5/2007 | Wang et al. |
| 7,292,257 B2 | | 11/2007 | Kang et al. |
| 7,332,890 B2 | | 2/2008 | Cohen et al. |
| 7,333,642 B2 | | 2/2008 | Green |
| 7,352,153 B2 | | 4/2008 | Yan |
| 7,363,121 B1 | | 4/2008 | Chen et al. |
| 7,467,211 B1 | | 12/2008 | Herman et al. |
| 7,483,867 B2 | | 1/2009 | Ansari et al. |
| 7,510,428 B2 | | 3/2009 | Obata et al. |
| 7,557,758 B2 | | 7/2009 | Rofougaran |
| 7,631,833 B1 | | 12/2009 | Ghaleb et al. |
| 7,657,560 B1 | | 2/2010 | Dirienzo |
| 7,703,113 B2 | | 4/2010 | Dawson |
| 7,737,993 B2 | | 6/2010 | Kaasila et al. |
| 7,861,366 B2 | | 1/2011 | Hahm et al. |
| 8,126,960 B2 | | 2/2012 | Obradovich et al. |
| 8,212,533 B2 | | 7/2012 | Ota |
| 8,320,534 B2 | | 11/2012 | Kim et al. |
| 8,374,171 B2 | | 2/2013 | Cho et al. |
| 8,400,491 B1 | | 3/2013 | Panpaliya et al. |
| 8,401,275 B2 | | 3/2013 | Wang et al. |
| 8,423,284 B2 | | 4/2013 | O'Shea |
| 8,442,661 B1 | | 5/2013 | Blackwell et al. |
| 8,451,731 B1 | | 5/2013 | Lee et al. |
| 8,515,577 B2 | | 8/2013 | Wang et al. |
| 8,610,786 B2 | | 12/2013 | Ortiz |
| 8,612,051 B2 | | 12/2013 | Norman et al. |
| 8,639,797 B1 | | 1/2014 | Pan et al. |
| 8,670,017 B2 | | 3/2014 | Stuart et al. |
| 8,726,454 B2 | | 5/2014 | Gilbert et al. |
| 8,836,751 B2 | | 9/2014 | Ballantyne et al. |
| 8,849,679 B2 | | 9/2014 | Wang et al. |
| 8,849,680 B2 | | 9/2014 | Wright et al. |
| 8,861,750 B2 | | 10/2014 | Roe et al. |
| 8,897,920 B2 | | 11/2014 | Wang et al. |
| 8,902,278 B2 | | 12/2014 | Pinter et al. |
| 2002/0109775 A1 | | 8/2002 | White et al. |
| 2002/0128985 A1 | | 9/2002 | Greenwald |
| 2003/0050734 A1 | | 3/2003 | Lapham |
| 2003/0112823 A1 | | 6/2003 | Collins et al. |
| 2003/0135097 A1 | | 7/2003 | Wiederhold et al. |
| 2003/0195662 A1 | | 10/2003 | Wang et al. |
| 2003/0216833 A1 | | 11/2003 | Mukai et al. |
| 2004/0008138 A1 | | 1/2004 | Hockley, Jr. et al. |
| 2004/0167668 A1 | * | 8/2004 | Wang .................. G06F 19/3418 700/248 |
| 2004/0218099 A1 | | 11/2004 | Washington |
| 2004/0260790 A1 | | 12/2004 | Balloni et al. |
| 2005/0024485 A1 | | 2/2005 | Castles et al. |
| 2005/0073575 A1 | | 4/2005 | Thacher et al. |
| 2005/0110867 A1 | * | 5/2005 | Schulz ................... H04N 7/142 348/14.05 |
| 2005/0125083 A1 | | 6/2005 | Kiko |
| 2005/0149364 A1 | | 7/2005 | Ombrellaro |
| 2005/0219356 A1 | * | 10/2005 | Smith ................. A47B 21/0073 348/14.05 |
| 2005/0264649 A1 | | 12/2005 | Chang et al. |
| 2005/0286759 A1 | | 12/2005 | Zitnick et al. |
| 2006/0056655 A1 | | 3/2006 | Wen et al. |
| 2006/0056837 A1 | | 3/2006 | Vapaakoski |
| 2006/0066609 A1 | | 3/2006 | Iodice et al. |
| 2006/0071797 A1 | | 4/2006 | Rosenfeld et al. |
| 2006/0224781 A1 | | 10/2006 | Tsao et al. |
| 2007/0093279 A1 | | 4/2007 | Janik |
| 2007/0116152 A1 | | 5/2007 | Thesling |
| 2007/0170886 A1 | | 7/2007 | Plishner |
| 2007/0226949 A1 | | 10/2007 | Hahm et al. |
| 2007/0290040 A1 | | 12/2007 | Wurman et al. |
| 2008/0051985 A1 | | 2/2008 | D'Andrea et al. |
| 2008/0091340 A1 | | 4/2008 | Milstein et al. |
| 2008/0161969 A1 | | 7/2008 | Lee et al. |
| 2008/0232763 A1 | | 9/2008 | Brady |
| 2008/0263628 A1 | | 10/2008 | Norman et al. |
| 2008/0267069 A1 | | 10/2008 | Thielman et al. |
| 2009/0049640 A1 | | 2/2009 | Lee et al. |
| 2009/0102919 A1 | | 4/2009 | Zamierowski et al. |
| 2010/0026239 A1 | | 2/2010 | Li et al. |
| 2010/0066804 A1 | | 3/2010 | Shoemake et al. |
| 2010/0171826 A1 | | 7/2010 | Hamilton et al. |
| 2010/0278086 A1 | | 11/2010 | Pochiraju et al. |
| 2010/0301679 A1 | | 12/2010 | Murray et al. |
| 2011/0022705 A1 | | 1/2011 | Yellamraju et al. |
| 2011/0071675 A1 | | 3/2011 | Wells et al. |
| 2011/0072114 A1 | | 3/2011 | Hoffert et al. |
| 2011/0193949 A1 | | 8/2011 | Nambakam et al. |
| 2011/0280551 A1 | | 11/2011 | Sammon |
| 2012/0059946 A1 | | 3/2012 | Wang |
| 2012/0113856 A1 | | 5/2012 | Krishnaswamy |
| 2012/0203731 A1 | | 8/2012 | Nelson et al. |
| 2012/0291809 A1 | | 11/2012 | Kuhe et al. |
| 2013/0250938 A1 | | 9/2013 | Anandakumar et al. |
| 2014/0047022 A1 | | 2/2014 | Chan et al. |
| 2014/0085543 A1 | | 3/2014 | Hartley et al. |
| 2014/0135990 A1 | | 5/2014 | Stuart et al. |
| 2014/0139616 A1 | | 5/2014 | Pinter et al. |
| 2014/0155755 A1 | | 6/2014 | Pinter et al. |

FOREIGN PATENT DOCUMENTS

| | | |
|---|---|---|
| CN | 1743144 A | 3/2006 |
| CN | 101049017 A | 10/2007 |

(56) References Cited

FOREIGN PATENT DOCUMENTS

CN           101151614 A      3/2008
CN           100407729 C      7/2008

OTHER PUBLICATIONS

ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.

Brenner, "A technical tutorial on the IEEE 802.11 protocol", BreezeCOM Wireless Communications, 1997, pp. 1-24.

Library of Congress, "008-Fixed-Length Data Elements (NR)", MARC 21 Format for Classification Data, downloaded from http://www.loc.gov/marc/classification/cd008.html, Jan. 2000, pp. 1-14.

Paulos, et al., "Personal Tele-Embodiment", Chapter 9 in Goldberg, et al., ed. "Beyond webcams", MIT Press, Jan. 4, 2002, pp. 155-167.

Paulos, "Personal tele-embodiment", OskiCat Catalog Record, UCB Library Catalog, 2001, 3 pages.

Paulos, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages, including 4 pages of e-mails.

Paulos, et al., "Social Tele-Embodiment: Understanding Presence", Autonomous Robots, vol. 11, Issue 1, Kluwer Academic Publishers, Jul. 2001, pp. 87-95.

Screenshot Showing Google Date for Lemaire Telehealth Manual, Screenshot Retrieved on Dec. 18, 2014, 2 page.

Nomadic Technologies, Inc., "Nomad Scout Language Reference Manual", Software Version: 2.7, Part No. DOC00002, Jul. 12, 1999, 47 pages.

Fulbright et al., "SWAMI: An Autonomous Mobile Robot for Inspection of Nuclear Waste of Storage Facilities", Autonomous Robots, vol. 2, 1995, pp. 225-235.

\* cited by examiner

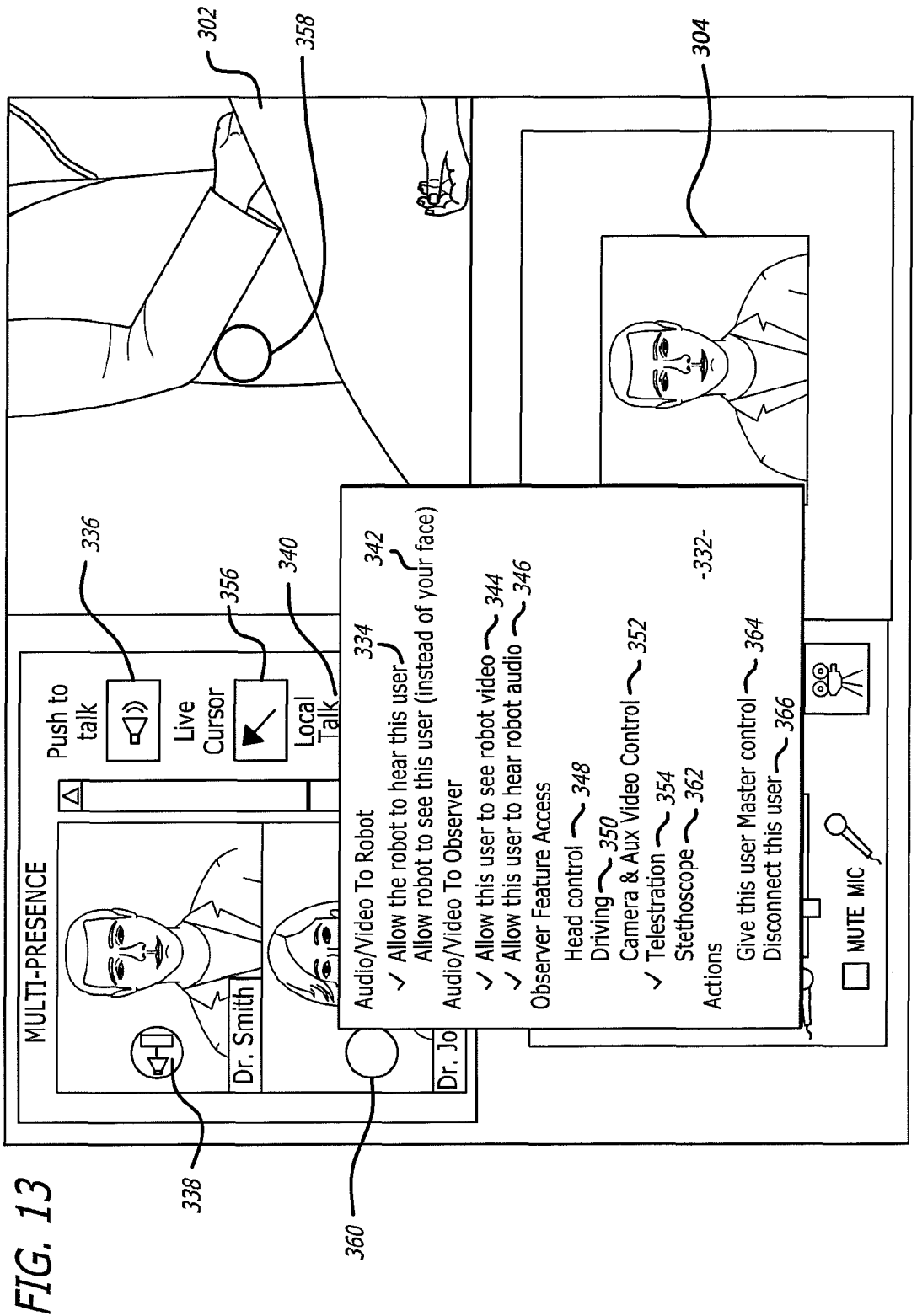

TELE-PRESENCE ROBOT SYSTEM WITH SOFTWARE MODULARITY, PROJECTOR AND LASER POINTER

BACKGROUND OF THE INVENTION

1. Field of the Invention

The subject matter disclosed generally relates to the field of robotics.

2. Background Information

Robots have been used in a variety of applications ranging from remote control of hazardous material to assisting in the performance of surgery. For example, U.S. Pat. No. 5,762, 458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile tele-presence robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones that allow for two-way video/audio communication. The robot camera provides video images to a screen at the remote station so that the user can view the robot's surroundings and move the robot accordingly.

BRIEF SUMMARY OF THE INVENTION

A remote control station accesses one of at least two different robots that each have at least one unique robot feature. The remote control station receives information that identifies the robot feature of the accessed robot. The remote control station displays a display user interface that includes at least one field that corresponds to the robot feature.

BRIEF DESCRIPTION OF THE DRAWINGS

FIG. 13 is an illustration of the user interface shown in FIG. 10 with a pull-down menu.

DETAILED DESCRIPTION

A remote control station accesses one of at least two different robots that each have at least one unique robot feature. The remote control station receives information that identifies the robot feature of the accessed robot. The remote control station displays a display user interface that includes at least one field that corresponds to the robot feature. The robot may have a laser pointer and/or a projector.

Figure 1:
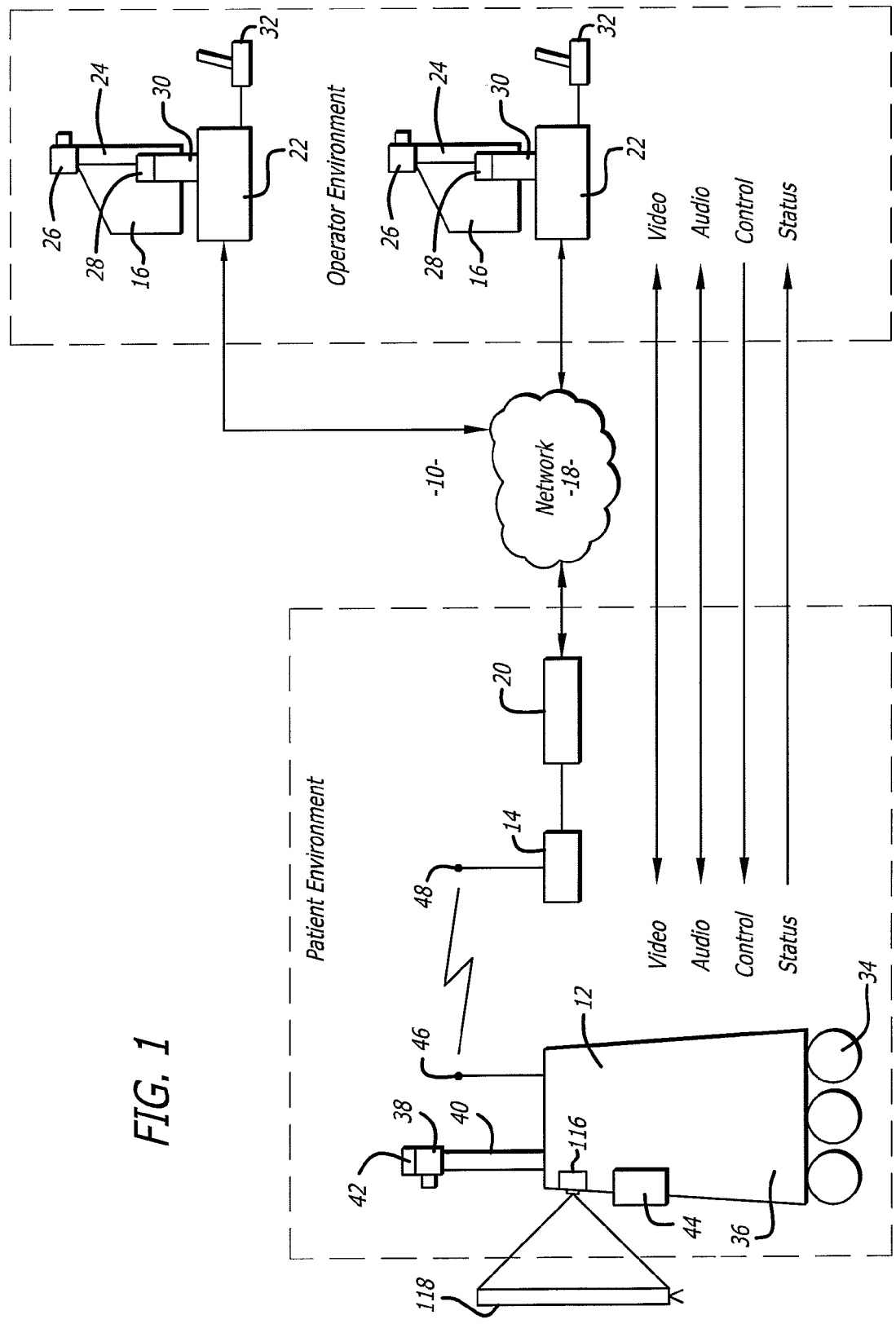
FIG. 1 is an illustration of a robotic system.

Referring to the drawings more particularly by reference numbers, FIG. 1 shows an embodiment of robot system 10. The robot system 10 includes a robot 12, a base station 14 and a plurality of remote control stations 16. Each remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

Each remote control station 16 may include a computer 22 that has a monitor 24, a camera 26, a microphone 28 and a speaker 30. The computer 22 may also contain an input device 32 such as a joystick or a mouse. Each control station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
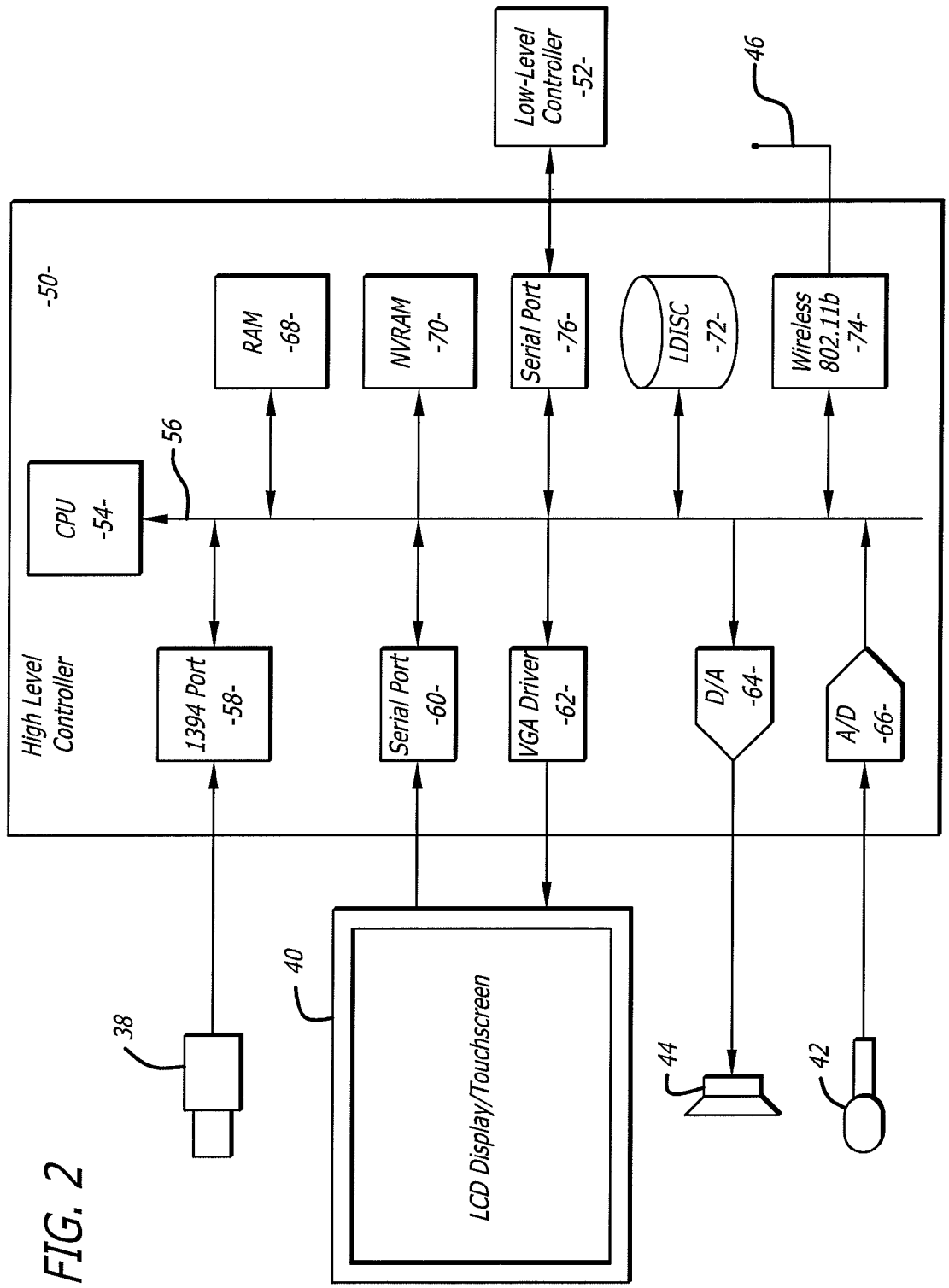
FIG. 2 is a schematic of an electrical system of a robot.

FIG. 2 shows an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to someone at the robot site and vice versa, or allow someone at the robot site to access the Internet. In general the high level controller 50 operates to control the communication between the robot 12 and the remote control station 16.

The high level controller 50 may be linked to the low level controller 52 by serial port 76. The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station. Although two controllers are shown, it is to be understood that the robot 12 may have one controller controlling the high and low level functions.

Figure 3:
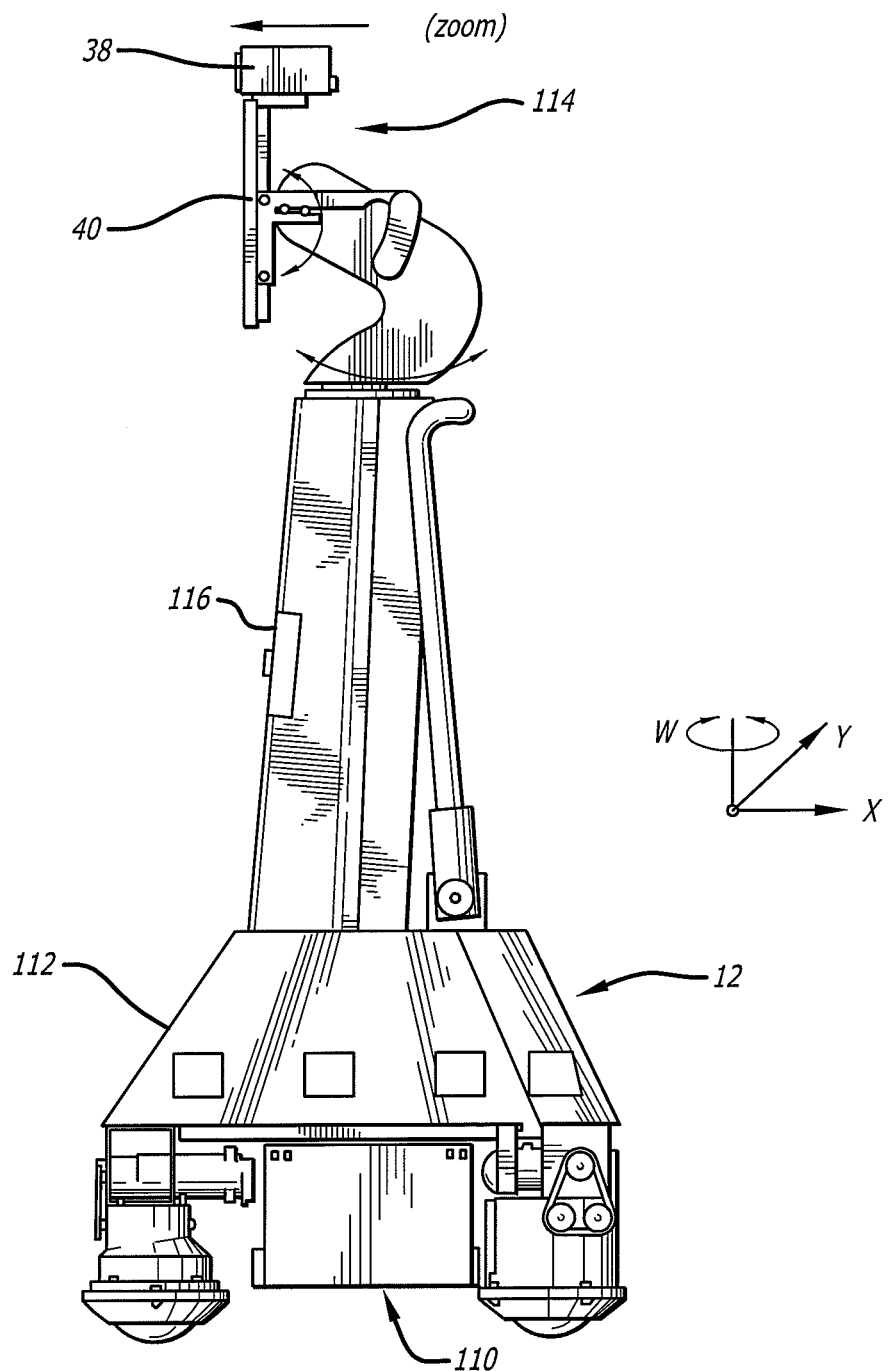
FIG. 3 is side view of the robot.

FIG. 3 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have a head 114 that supports the camera 38 and the monitor 40. The head 114 may have two degrees of freedom so that the camera 26 and monitor 24 can swivel and pivot as indicated by the arrows.

As shown in FIGS. 1 and 3, a projector 116 may be embedded into the robot 12. The projector 116 can project images transmitted from the remote control station 16 or another source such as an external server. Although an embedded projector is described, the projector 116 may be an external device that is plugged into an auxiliary port of the robot. The projector 116 can project an image onto a screen 118 so that viewers at the robot site can view the projected image. Consequently, a user at the remote control station can transmit information to the robot that is then projected by the projector 116. For example, the information may be a PowerPoint presentation that is displayed by the robot projector 116 and allows the remote control station user to conduct a remote meeting.

Figure 4:
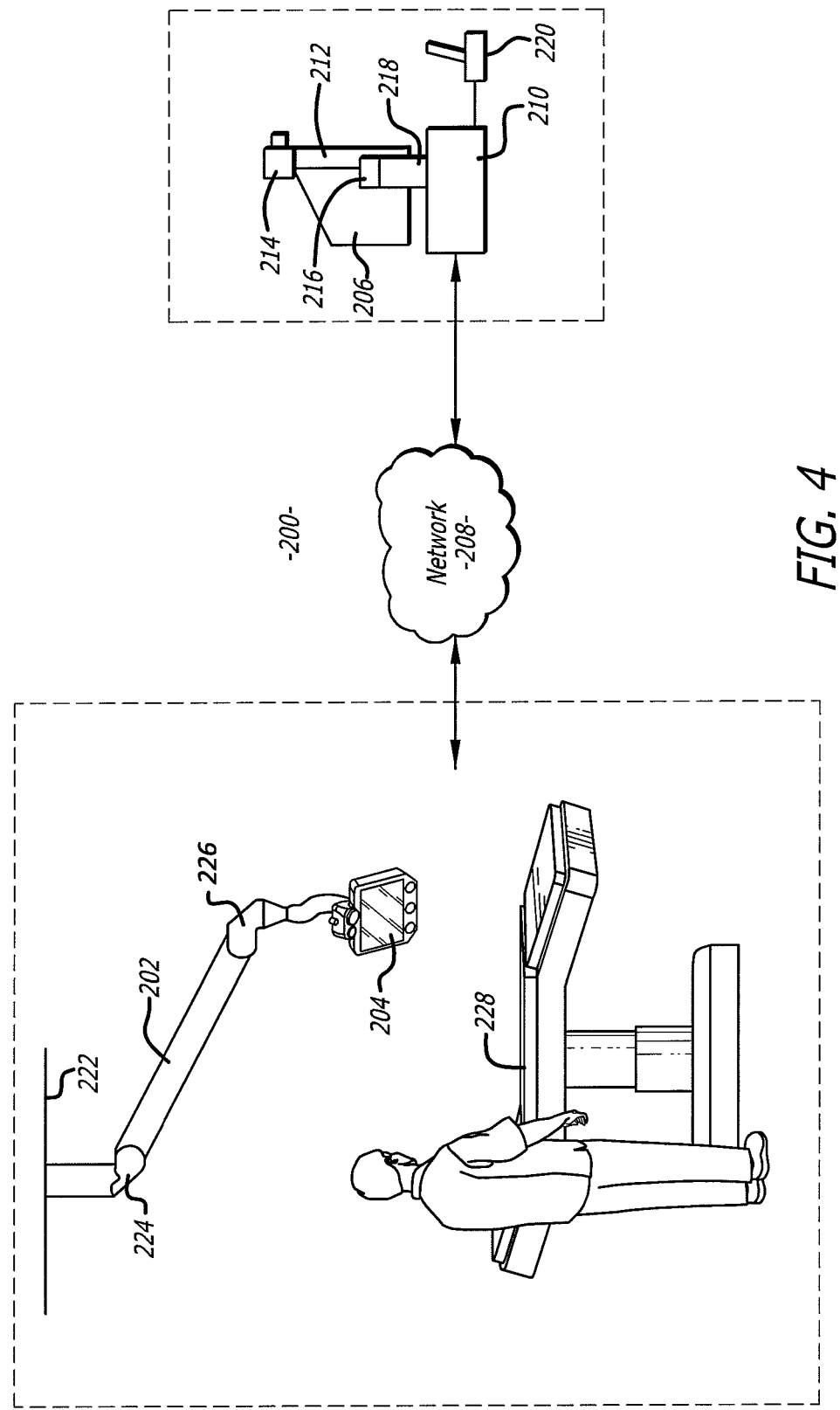
FIG. 4 is an illustration of a tele-presence system.
Figure 5:
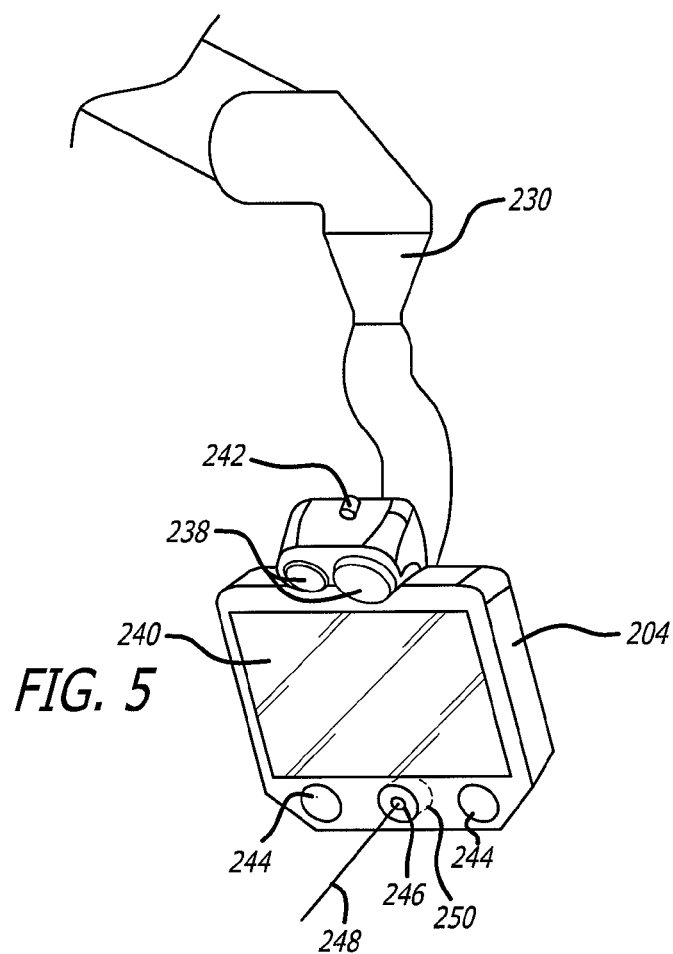
FIG. 5 is an enlarged view of a robot face of the system.
Figure 6:
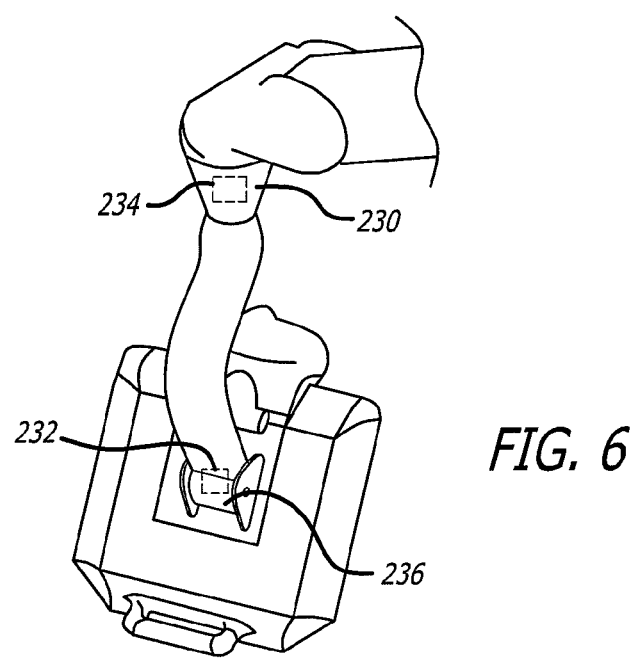
FIG. 6 is a rear view of the robot face.

Referring to the drawings more particularly by reference numbers, FIGS. 4, 5 and 6 show an alternate tele-presence system 200. The system 200 includes a boom 202, a robot face 204 and a remote control station 206. The remote control station 206 may be coupled to the robot face 204 through a network 208.

The remote control station 206 may include a computer 210 that has a monitor 212, a camera 214, a microphone 216 and a speaker 218. The computer 210 may also contain an input device 220 such as a joystick or a mouse. The control station 206 is typically located in a place that is remote from the robot face 204. Although only one remote control station 206 is shown, the system 10 may include a plurality of remote stations 206. In general any number of robot faces 204 may be coupled to any number of remote stations 206 or other robot faces 204. For example, one remote station 16 may be coupled to a plurality of robot faces 204, or one robot face 204 may be coupled to a plurality of remote stations 206, or a plurality of robot faces 204. The system may include an arbitrator (not shown) that control access between the robot face(s) 204 and the remote stations 206.

The boom 202 may extend from the ceiling 222 of a medical facility. The boom 202 may include articulate joints 224 and 226 that provide at least two degrees of freedom and allow a user to move the robot face 204 relative to an medical table 228 such as an operating room ("OR") table.

The boom 202 may have additional joints 230 and 232 that allow the robot face 204 to be panned and tilted, respectively. The joints 230 and 232 may contain actuators 234 and 236, respectively, that can be remotely actuated through manipulation of the input device 220 at the remote station 206.

Each robot face 204 includes a camera(s) 238, a monitor 240, a microphone(s) 242 and a speaker(s) 244. The robot camera 238 is coupled to the remote monitor 212 so that a user at the remote station 206 can view a patient on the table 228. Likewise, the robot monitor 240 is coupled to the remote camera 214 so personnel at the surgical site may view the user of the remote station 206. The microphones 216 and 242, and speakers 218 and 244, allow for audible communication between the system operator and the personnel at the surgical site.

The robot face 204 may have an embedded laser pointer 246 that emits a laser 248. The laser pointer 246 can be turned on and controlled thru the remote control station 206. The laser pointer 246 may include an actuator(s) 250 that provides an additional degree(s) of freedom for the pointer. The laser pointer 246 may also integrate into the mobile robot shown in FIGS. 1 and 3.

The system 200 allows a system user such as a surgical specialist to view a patient on the table 228 and provide remote medical consultation through the remote station and the robot face 204. Personnel at the surgical site can transmit questions and responses through the system back to the system operator. The robot camera 238 allows the specialist to view the patient and enhance the medical consultation. The robot monitor 240 can display the specialist to provide a feeling of presence at the surgical site. The boom 202 allows the personnel to move the robot face 204 into and out of the surgical area. The remote user can move the robot face so that the robot camera faces the patient and then the doctor at the surgical site to allow the remote user to observe the patient and provide consultation to the doctor.

The robot face 204 can be retrofitted onto booms that presently exist in medical facilities. For example, some present medical facilities include a monitor attached to a boom. The existing monitor can be replaced with the robot face 14 that is then coupled to the remote station 16.

Figure 7:
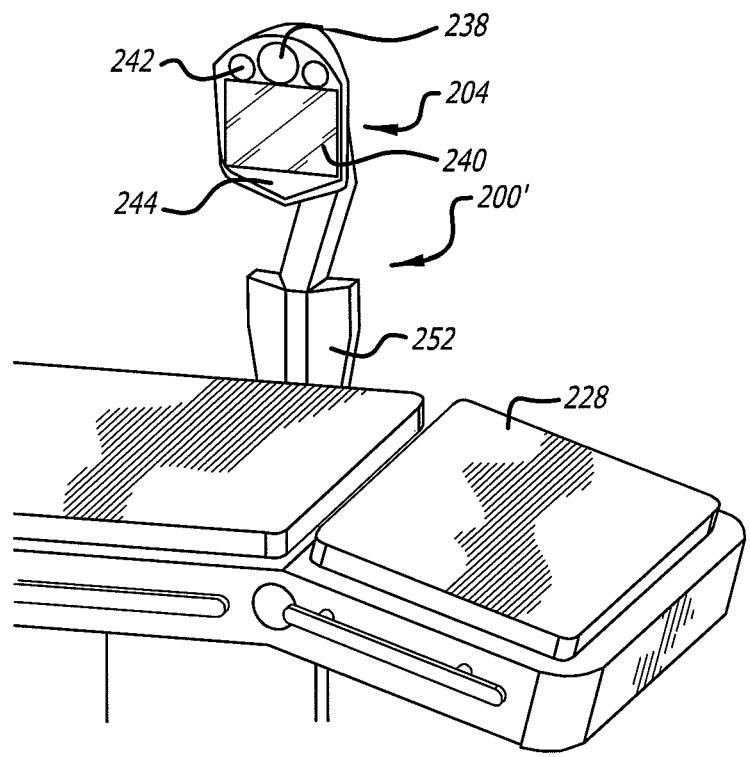
FIG. 7 is an illustration of an alternate embodiment of the tele-presence system.
Figure 8:
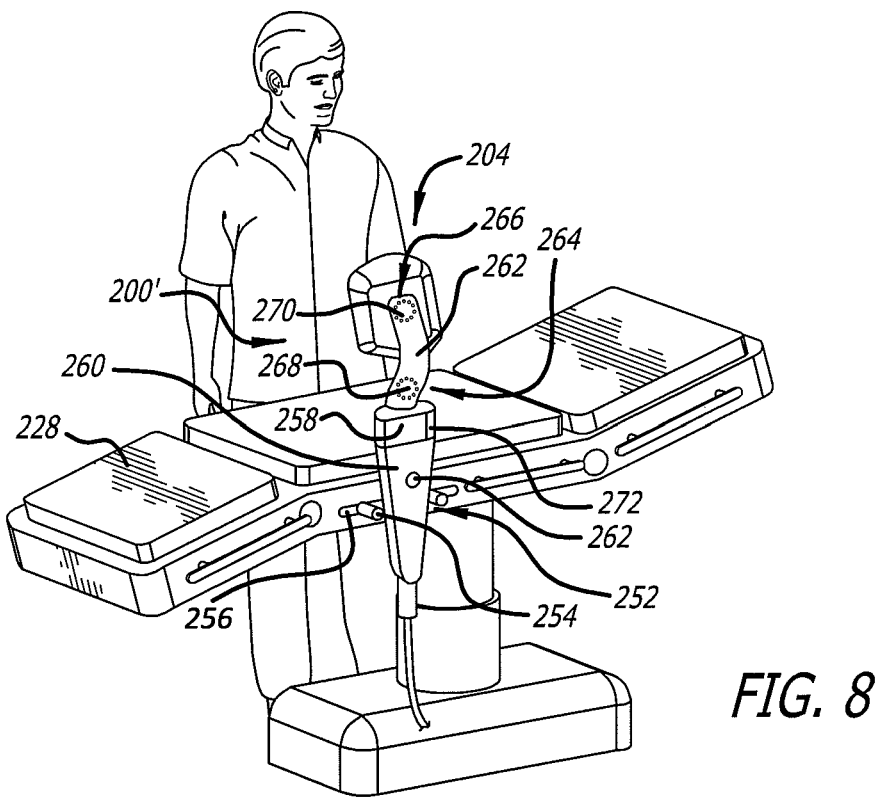
FIG. 8 is a rear view of a robot face of the embodiment shown in FIG. 7.

FIGS. 7 and 8 shows an alternate embodiment of a system 200' where the robot face 204 is attached to the table 228 with an attachment mechanism 252. The robot face 204 may or may not have a laser pointer. The attachment mechanism 252 may include a pair of clamps 254 that are pressed into a rail 256 of the table 228. The attachment mechanism 252 may have a sleeve 258 that slides relative to a housing 260 so that a user can adjust the height of the robot face 204. The face position may be locked in place by rotation of knob 262.

The attachment mechanism 252 may include a neck portion 262 with joints 264 and 266 that allow for pan and tilt of the robot face 204, respectively. The joints 264 and 266 may be manually actuated or contain actuators 268 and 270, respectively, that can be actuated through the input device 220 at the remote station 206.

The attachment mechanism 252 may include handles 272 that allow a user to carry the robot face 204 to and from the table 228. The attachment mechanism 252 allows the robot face 204 to be readily utilized at a surgical site, particularly when the operating room does not have a boom.

The various robot systems shown and described may have certain components and software that are the same or similar to a robotic system provided by the assignee InTouch Technologies, Inc. of Santa Barbara, Calif. under the name RP-7 and embodies a system described in U.S. Pat. No. 6,925,357, which is hereby incorporated by reference.

In operation, the robot 12 may be placed in a home, public or commercial property, or a facility where one or more patients are to be monitored and/or assisted. The facility may be a hospital or a residential care facility. By way of example, the robot 12 may be placed in a home where a health care provider may, monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home, property or facility by manipulating the input device 32 at a remote station 16.

The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | |
|---|---|---|---|---|---|
| | Local | Caregiver | Doctor | Family | Service |
| Current User Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |

TABLE II-continued

| | | Requesting User | | | |
|---|---|---|---|---|---|
| | Local | Caregiver | Doctor | Family | Service |
| Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 9:
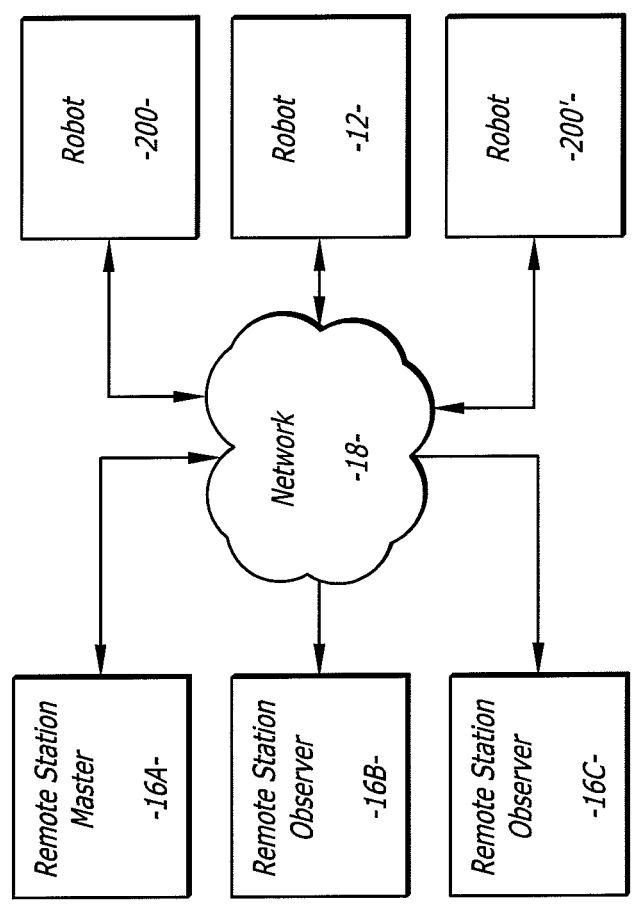
FIG. 9 is a schematic of a robotic system wherein multiple remote stations are coupled to the robot.

FIG. 9 shows a system with a plurality of remote stations 16A, 16B and 16C that can access different robots 12, 200 and 200' through the network 18. The system can be set into a session mode wherein a master remote station 16A controls movement of a robot 12, 200 or 200' and receives both video and audio information from the robot camera and speaker, respectively. The observer stations 16B and 16C may also receive audio and visual information transmitted between the robot 12, 200 or 200' and the station 16A. This mode allows multiple users at stations 16B and 16C to observe use of the robot while a teacher or master at station 16A moves the robot.

During a session the master remote station 16A can retransmit the audio/visual information received from a robot 12, 200 or 200' to the observer stations 16B and 16C. This can be done by changing the ID(s) in the ID field of the data packets received from the robot and then retransmitting the packets to the observer stations. Alternatively, the master remote station 16A can instruct the robot to transmit the audio and visual information to the master 16A, and the observer 16B and 16C remote stations. It being understood that each remote station 16A, 16B and 16C has a unique network identifier such as an IP address that allows the robot to direct information to each station. The packets may contain a BROADCAST field that contains the station IDs for the remote stations that are to receive packets from the robot. The BROADCAST field may be filled by the master station 16A.

The session mode allows for training through the robot. For example, the master remote station 16A may be operated by a physician who moves the robot into visual and audio contact with a patient. The observer remote stations 16B an 16C may be manned by personnel such as interns that observe and receive instructional training on providing care giving to the patient. Although instruction of medical personnel is described, the system can be used to train any, group of users that are remotely located from a training area. For example, the system may be used to train personnel at a department store or allow potential buyers of real estate property to remotely view the property.

Figure 10:
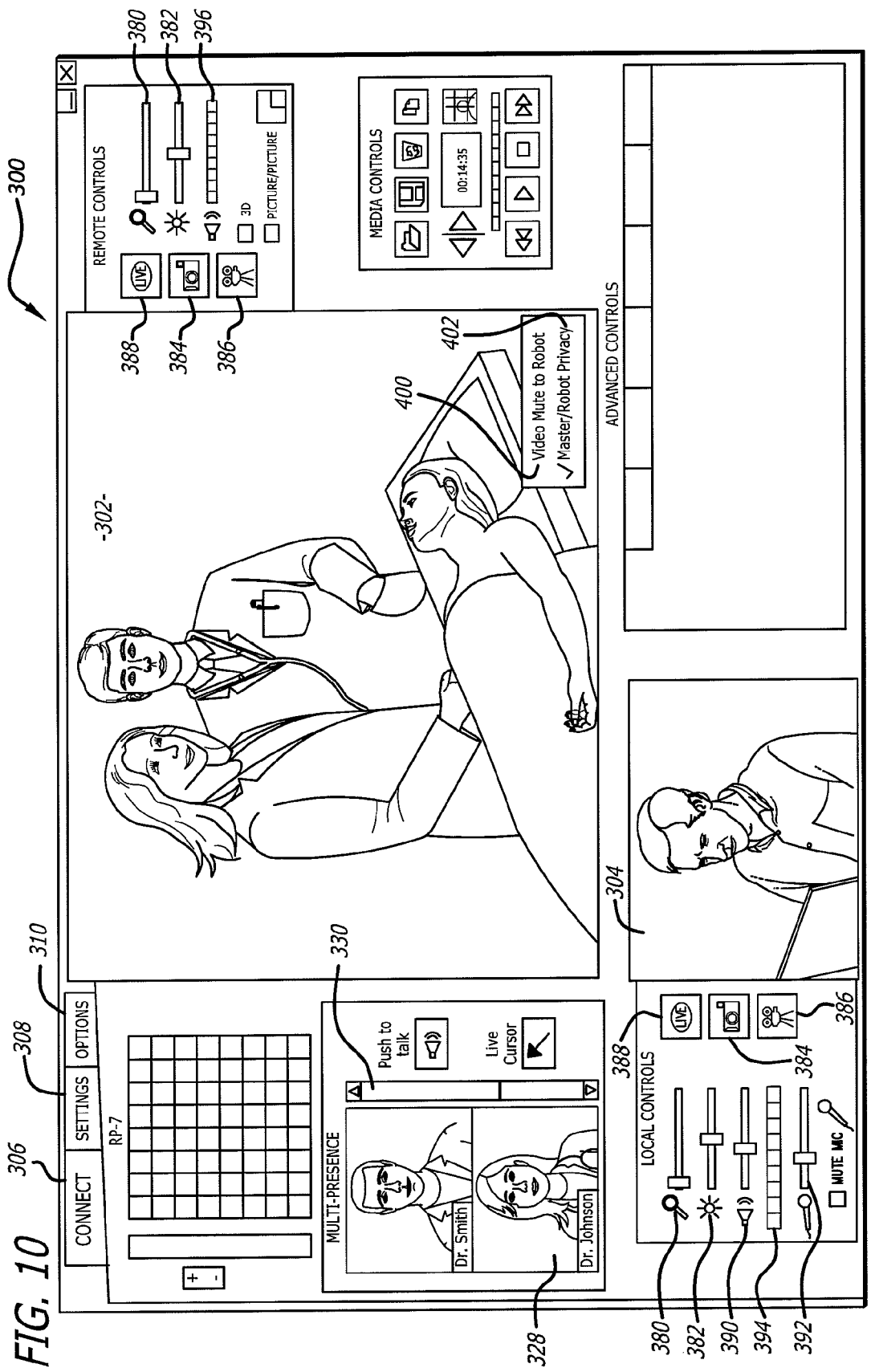
FIG. 10 is an illustration of a user interface.

FIG. 10 shows a display user interface ("DUI") 300 displayed at the master control station 16A. The DUI 300 may include a robot view field 302 that displays a video image captured by the camera of the robot. The DUI 300 may also include a station view field 304 that displays a video image provided by the camera of the master remote station 16A. The DUI 300 may be part of an application program stored and operated by the computer 22 of the remote station 16A.

The DUI 300 may include a "Connect" button 306 that can be selected to connect the station to a robot. Selection of the Connect button 306 may cause the display of pull-down screens, etc. that allow the user to select a desired robot. System settings and options can be selected through buttons 308 and 310, respectively.

Figure 11:
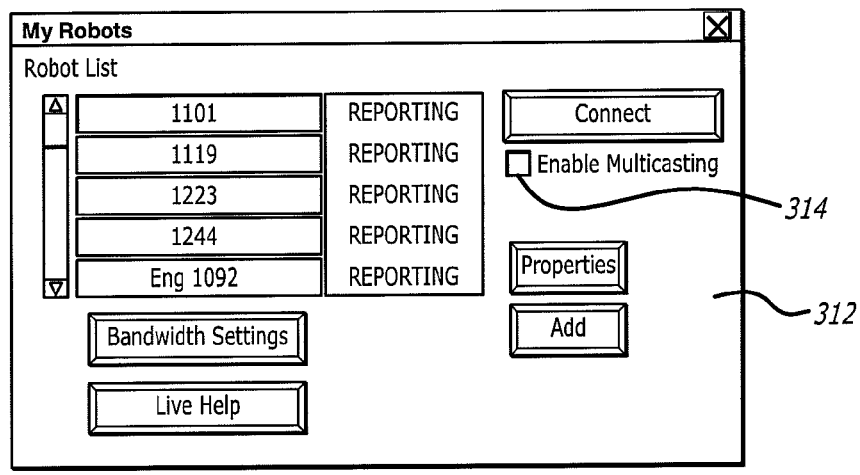
FIG. 11 is an illustration of a message popup of the user interface.

One of the options is to allow for multicasting. FIG. 11 shows a menu 312 with an "Enable Multicasting" box 314 that can be "checked" to allow for other remote station to join a multi-cast session.

Figure 12A:
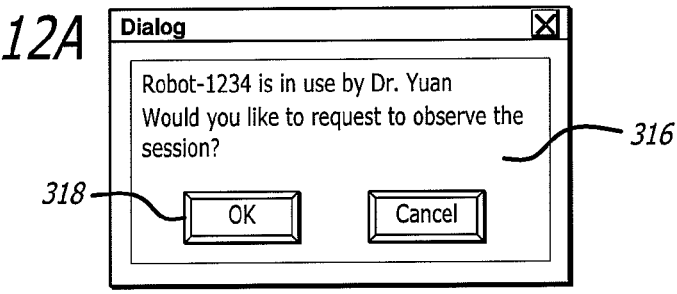
FIGS. 12A-C are illustrations of graphical messages.
Figure 12B:
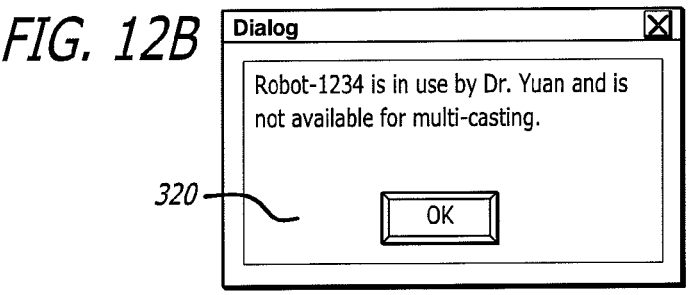
Figure 12C:
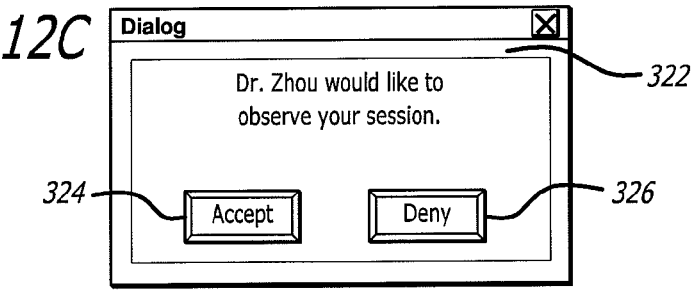

A user at an observer station may attempt a connection with the same robot. If a robot is already in use the screen may display a message box 316 as shown in FIG. 12A. The message box 316 includes an "OK" button 318 that allows the user to request joining the session as an observer. If the user presently connected to the robot has not enabled the multicasting feature then a message 320 may be displayed indicating this fact as shown in FIG. 12B. If the user selected the OK button 318 then the master user may receive the message 322 shown in FIG. 12C. The message includes an "Accept" button 324 and a "Deny" button 326 that allows the master user to accept or deny the request to observe the session, respectively. When an observer is accepted the observers may receive the audio/video feeds from by the robot.

User's that are accepted are displayed in an observer view field 328 of the master control station DUI 300 shown in FIG. 10. The field 328 can provide video images of the users captured by the cameras of the observer remote control stations. Each video image may also include a caption of the observer's name. The field includes a scroll down tab 330 that allows the master user to scroll down the video images of the observers.

The master user can right click on any observer video image to display the pull down menu 332 shown in FIG. 13. The pull down menu 328 allows the master user to select various options for the selected observer. The pull down menu 332 includes an "Allow The Robot To Hear This User" feature 334 that can be selected so that the observer can provide audio to the robot. The system may allow for simultaneous three way audio between the robot/master user and one observer. Both the master and the observer stations include a "Push To Talk" icon 336. If there is more than one observer then the "Push To Talk" icon 336 is enabled and the observer must continuously select the icon 336 to talk, much like a walkie-talkie button. The space bar may also be pushed after the icon 336 is selected to allow audio communication to the robot. When Push To Talk is selected then an icon 338 can be displayed in the observers video image to indicate which observer is providing audio input to the robot. The master and observer stations may also have a "Local Talk" icon 340. Selecting the Local Talk icon allows for textual communication between just the remote stations, popping up a text chat dialog box within each interface, which allows the master and observers to exchange text messages. Prior to displaying the text chat dialog box, a popup dialog box (not shown) may be displayed to the user who initiated Local Talk, which would list all current session participants, and allow the user to select only those participants to be part of the Local Talk. There may be a "Limit Voice" box (not shown) that can be selected to limit audio output of participants in the local chat to only those other remote stations participating in the local chat.

An "Allow Robot To See This User" feature 342 can be selected so that the observer's video image is provided to the monitor of the robot instead of the master user's video image. The observer's video image may be displayed in the station view field 304 when that observer's image is provided to the robot. The "Allow This User To See Robot Video" 344 and "Allow This User To Hear Robot Audio" features 346 can be selected so that the observer receives the video and audio feeds from the robot, respectively.

The "Head Control" feature 348 allows the selected observer to control the robot head to move the robot camera. The "Driving" feature 350 allows the observer to drive the robot. When the Driving feature is selected robot data such as position sensor data, battery power, etc. are provided to the selected observer's remote station. The "Camera & Aux Video Control" feature 352 allows the observer to control robot camera functions such as zoom, brightness, etc. The master no longer has the head, driving and camera controls when these features are transferred to an observer.

The menu 332 includes a "Telestration" feature 354 that allows an observer to annotate an image provided by to robot. For example, the image can be a document or an X-ray. An observer can annotate the image, for example to circle and area of the X-ray to help communicate with a patient at the robot site. The master or any observer can enable a cursor function by selecting a "Live Cursor" icon 356. Selecting the icon 356 allows the user to move a cursor 358 that is overlayed on the robot video image. The cursor 358 is provided on the image field 302 for all remote stations in a session. The master and observers can each be designated a different color so that different cursors can be distinguished by the users. The cursor color 360 can be displayed in the video image of the master or the observer.

The robot may connected to a medical instrument such as a stethoscope. The "Stethoscope" feature 362 of the pull down menu 332 allows the observers to receive instrument input from the stethoscope. The menu 332 may have a "Give This User Master Control" feature 364 that allows the selected observer to become a master user. The master can also disconnect an observer by selecting the "Disconnect This User" feature 366.

Figure 14:
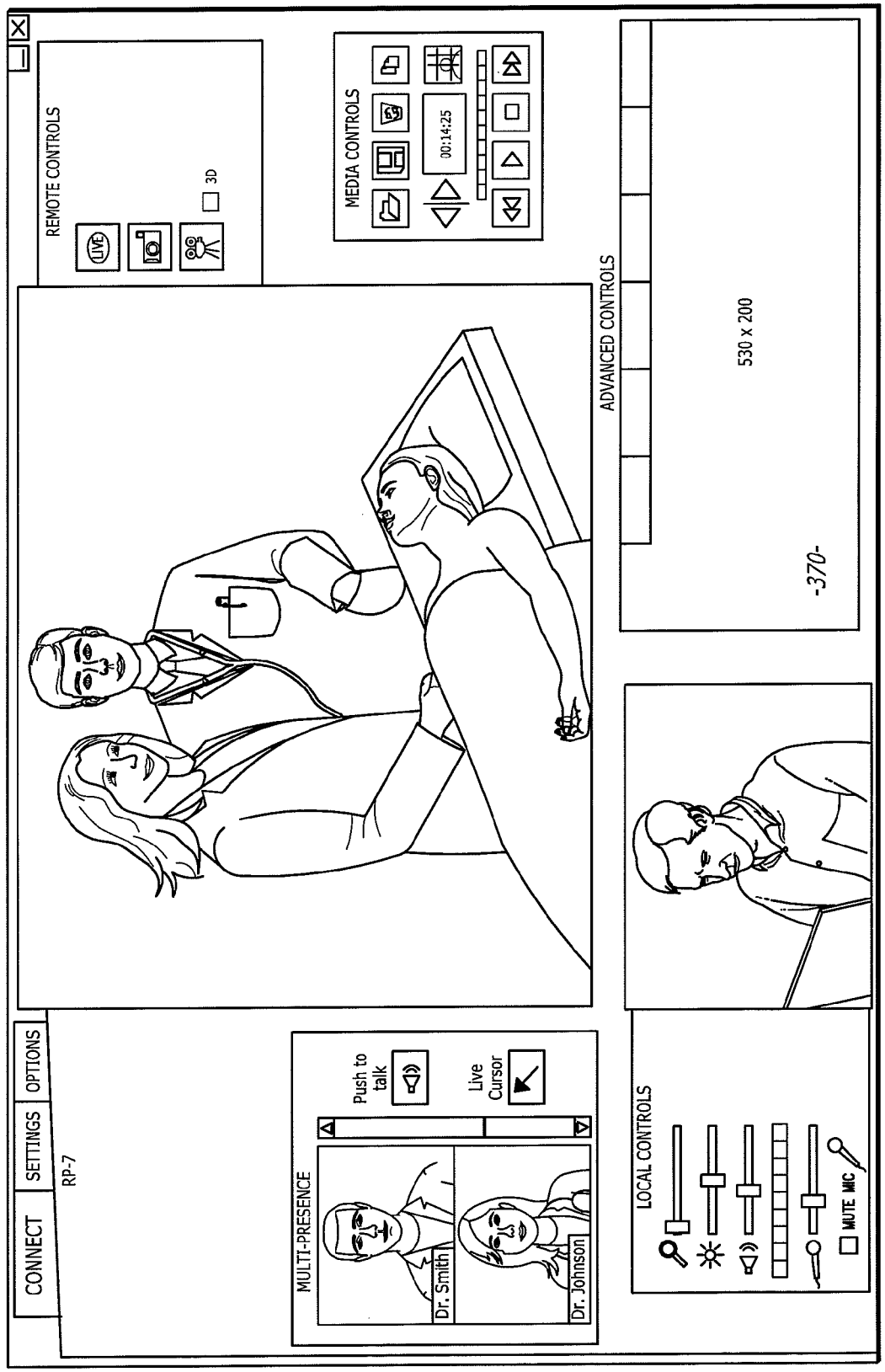
FIG. 14 is an illustration showing a user interface for an observer remote control station.

FIG. 14 shows a user interface 370 for observer. The interface does not include robot control functions unless enabled by the master user. The interface 370 is similar to the master DUI 300, but lacks certain robot controls.

Referring again to FIG. 10, both the robot view field 302 and the station view field 304 may have associated graphics to vary the video and audio displays. For example, each field may have graphical slide bars 380 and 382 to vary the zoom and brightness of the cameras, respectively. A still picture may be taken at either the robot or remote station by selecting one of the graphical camera icons 384. The still picture may be the image presented at the corresponding field 302 or 304 at the time the camera icon 384 is selected. Capturing and playing back video can be taken through graphical icons 386. A return to real time video can be resumed, after the taking of a still picture, captured video, or reviewing a slide show, by selecting a graphical LIVE button 388.

Figure 15:
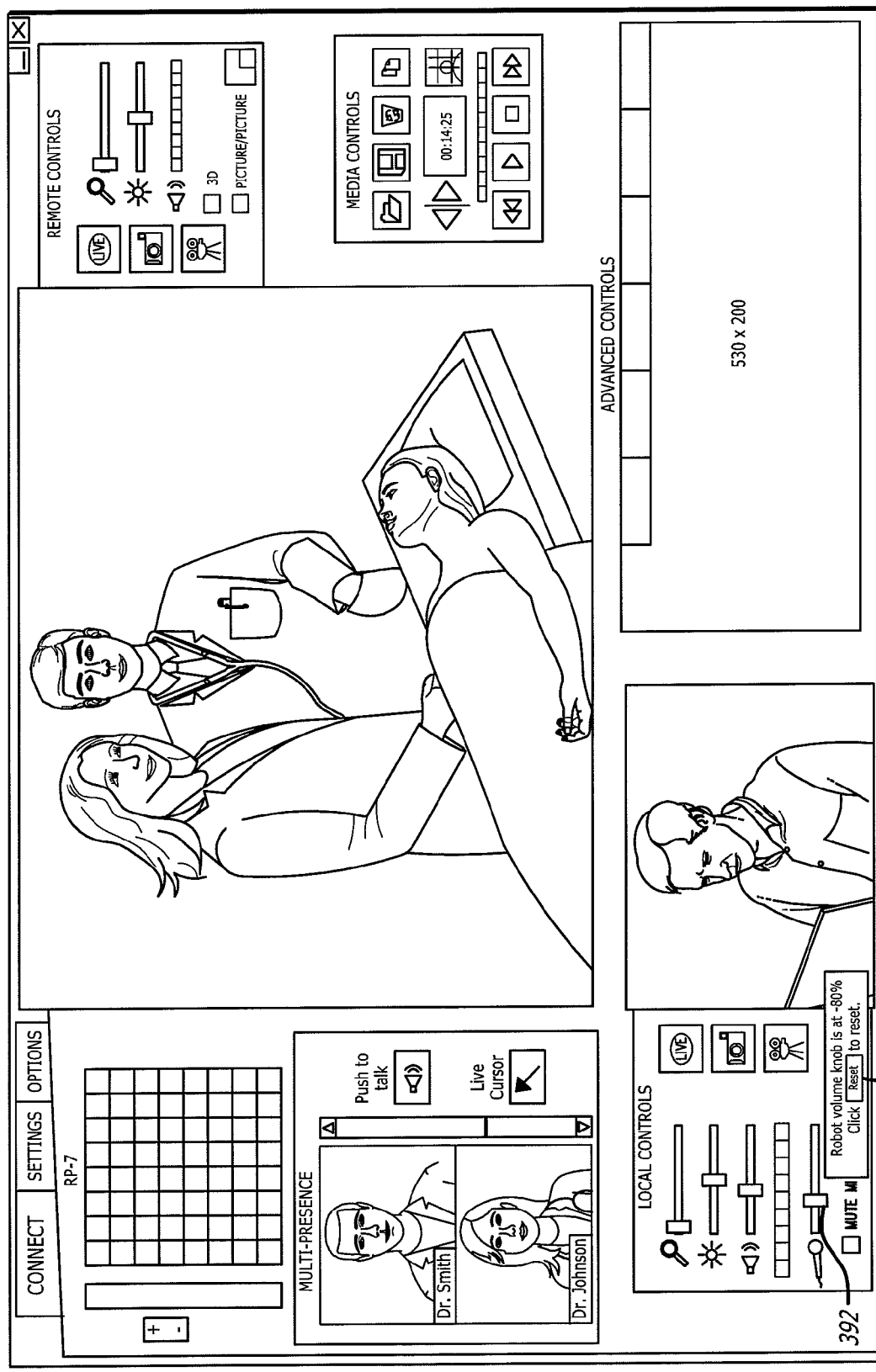
FIG. 15 is an illustration similar to FIG. 10 showing microphone volume control features.

The local controls can include slide bars for the local station speaker 390 and microphone 392. Also displayed is a microphone meter icon 394 that varies with the volume of the user's voice. The robot volume may be different from the user's input volume. The remote controls also includes a microphone meter icon 396 that represents the user's audio volume at the robot. The robot may have a local volume control so that user's at the robot site can vary the robot speaker volume. Normally the meter icons 394 and 396 will represent essentially the same value. The robot volume may be different from the user's input volume, for example, if the robot local volume control is adjusted the at the robot site. As shown in FIG. 15, if this occurs the volume slide bar 392 may be enabled to allow the user to vary the microphone. The DUI may also display a "Reset" button 398 that can be selected to automatically reset the robot speaker volume to a center position.

Referring to FIG. 10, the robot view field 302 may include a "Video Mute To Robot" feature 400 which when selected prevents audio and video transmission to the robot from all remote stations. Field 302 may also have a "Master/Robot Privacy" feature 402 that can prevent the observer stations from receiving robot video and audio from both the robot and the master control station.

Figure 16:
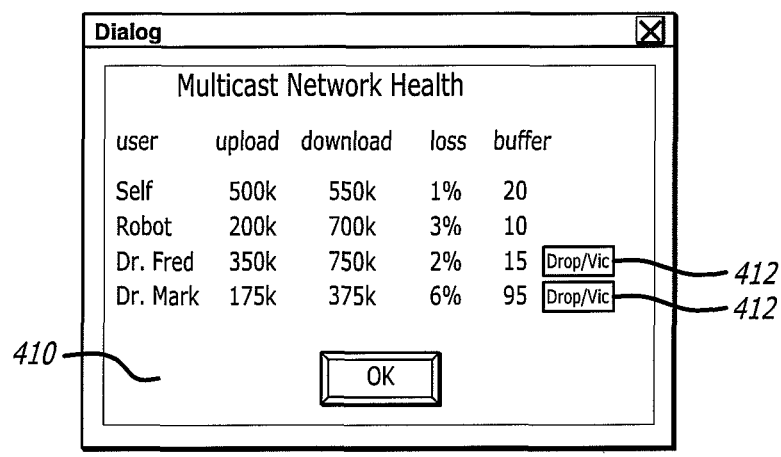
FIG. 16 is an illustration of a dialog box showing bandwidth requirement of the system during a session.

The master user can also be allowed to control the bandwidth of the system by controlling the video feeds to the observer stations. FIG. 16 shows a dialog box 410 that displays the bandwidth usage of various participants in a session, along with network health parameters such as packet losses and jitter between participants. "Drop Vid" buttons 412 may be placed next to observer stations so that the master user can drop a particular observer's video.

The system may have numerous applications. For example, a physician intensivist may initiate a remote presence session with a robot in order to diagnose a patient in an Emergency Room. Upon examining the patient, the physician may realize that the patient assessment will require consultation by a neurology specialist. The intensivist calls the neurologist by phone, asking him to join the session. Upon receiving the telephone request, the neurologist opens his laptop, selects the robot in question from the robot list in the interface, and clicks "Connect". Seeing the message in FIG. 7A, he clicks "OK" and then sees the message in FIG. 7B. The intensivist meanwhile sees the message in FIG. 7C and clicks "Accept". At this point the neurologist receives the robot video and can hear both the robot-side audio and the intensivist.

The intensivist uses the Live Cursor to point to the patient's face and EEG data on a wall. The neurologist obtains background information that can be provided by a nurse standing next to the patient and in front of the robot, as well as ICU-specific information provided by the intensivist on the master control station. Then, the neurologist can provide an audio assessment of the patient's condition. The intensivist then right-clicks on the thumbnail image of the neurologist in field 288, and clicks the appropriate features in the pull-down menu to allow the neurologist to be seen and heard on the robot. The neurologist can then inform both the patient and family of the condition.

In another application, a surgeon may be logged onto a robot and performing rounds in patient rooms within a hospital. Residents from hospitals in other cities join the session in the manner described above. The surgeon describes what he is doing to the residents, who may ask questions, and thereby learn the best way to round patients.

In another application, a hospital CEO may connect to the robot, and telephones three prospective doctors whom the hospital is courting to join the staff. These doctors each join the session as discussed above. The CEO then uses the joystick to drive the robot through the hospital, performing a virtual tour, and discusses the facility with the observer physicians.

In yet another application, a sales VP of an MRI manufacturing company may connect to a robot in the laboratory wing of a hospital, and then phones the COO of a different hospital to join the session. Upon joining, the sales VP drives the robot into the MRI lab and drives around the MRI machine, describing its features. An on-site MRI technician operates certain controls on the direction of the sales VP. The sales VP explains to the COO the various benefits of purchasing the MRI machine.

The system may be made so that the DUI displayed by the remote station corresponds to the robot embodiment, robot features and/or devices attached to the robot. For example, when accessing a mobile robot the DUI will display graphics associated with a mobile robot. These same graphics are not displayed when the remote station accesses a non-mobile robot such as that shown in FIGS. 4-8. If a robot has wireless transmission and/or runs on batteries, then the DUI would display a wireless signal strength indicator and battery level, respectively. For a robot that does not have wireless transmission or run on batteries the DUI would not display this information.

The remote control station software platform incorporates subclasses for robot features. For example, the subclasses may include identification of a mobile platform, wireless robot connection, battery powered robot, laser pointer, connected devices such as a projector or a medical instrument. The software may include a software object for each subclass. The robot provides its particular subclasses to the remote control station. This may be before, during, or after the remote control station accesses the robot. The subclasses for a particular robot may also be provided by a server. Upon connection the remote control station software instantiates and initializes objects for all the reported subclasses. The software can then perform iterations to determine certain features and selected functions for each object.

Figure 17:
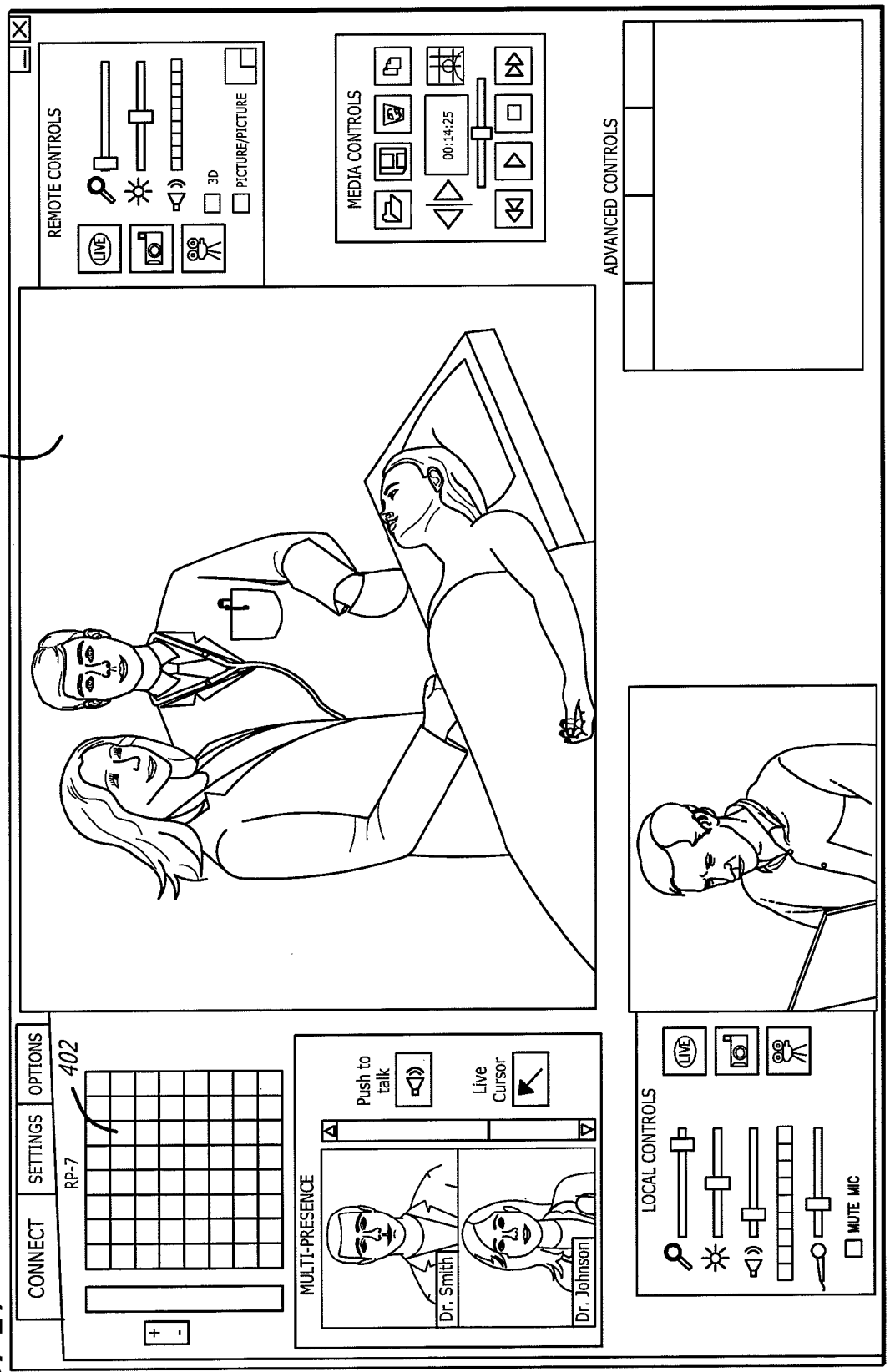
FIG. 17 is an illustration of a user interface for a mobile robot.

FIG. 17 is an embodiment of a DUI 400 for a remote station that is connected to a mobile robot similar to the robot disclosed and shown in FIGS. 1 and 3, but without the projector. Because the robot is mobile the DUI includes a graphical icon 402 that depicts the robot platform and any sensor data detected by the robot sensors. The graphical icon 402 is created by a software object that corresponds to a subclass provided by the robot.

Figure 18:
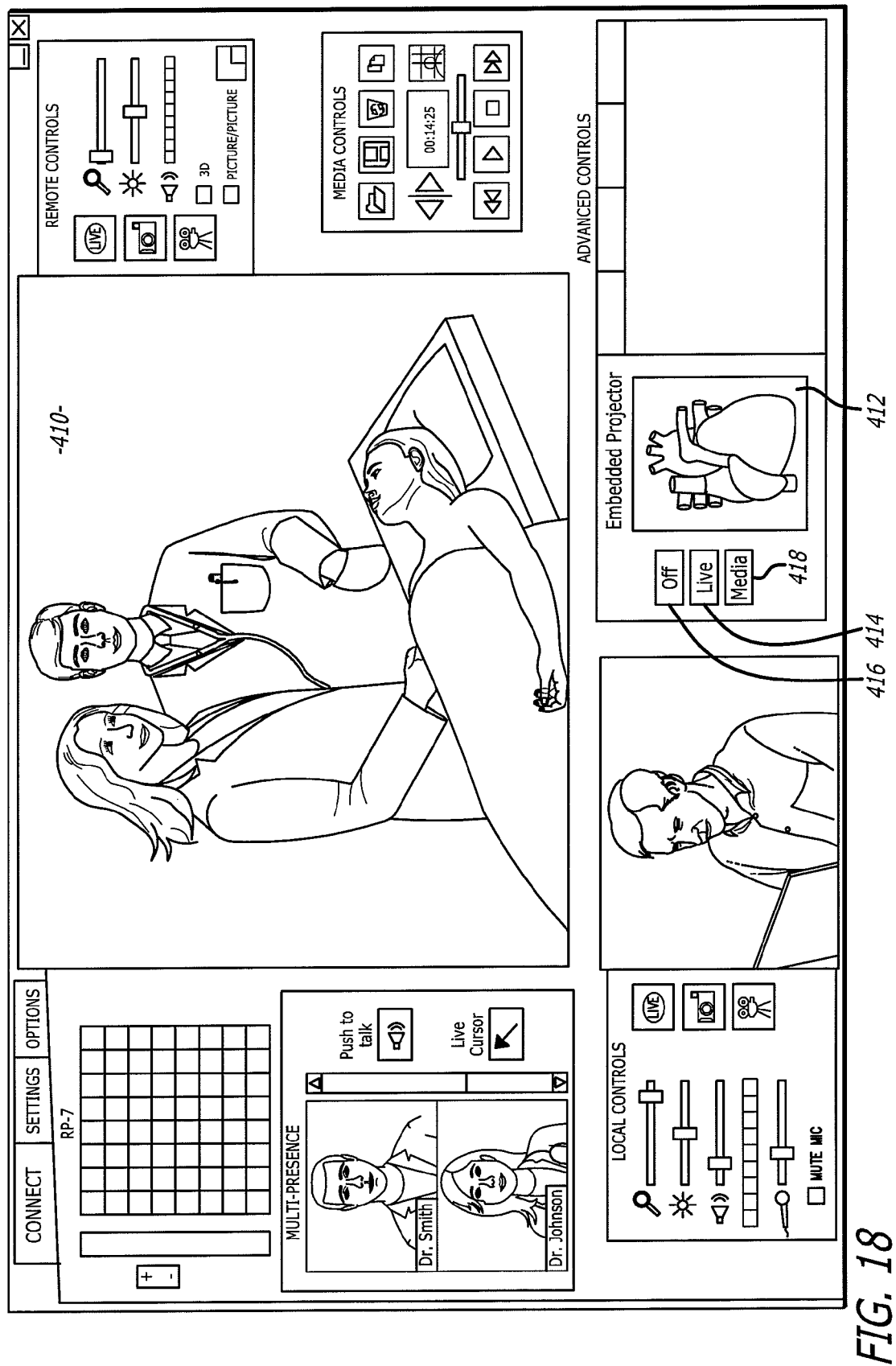
FIG. 18 is an illustration of a user interface for a mobile robot with a projector.

FIG. 18 is an embodiment of a DUI 410 for a remote station that is connected to a mobile robot that includes a embedded projector as shown in FIG. 1. The DUI includes a projector field 412 for the image projected by the robot projector. The projector field 412 is included because the robot has a subclass that corresponds to an object which creates the field 412. The projector field 412 may include a LIVE graphical button 414 that provides the projected image when selected and an OFF button 416 that can be selected to discontinue projection of the image. The DUI 410 may be adapted so that when a SHARE graphical button is selected (not shown) a pop-appears that allows a user to select between displaying an image on the robot monitor or projecting the image thru the projector. If the later is selected the image is projected by the robot projector and shown in the projector field 412. A mode button 418 is then changed to MEDIA.

Figure 19:
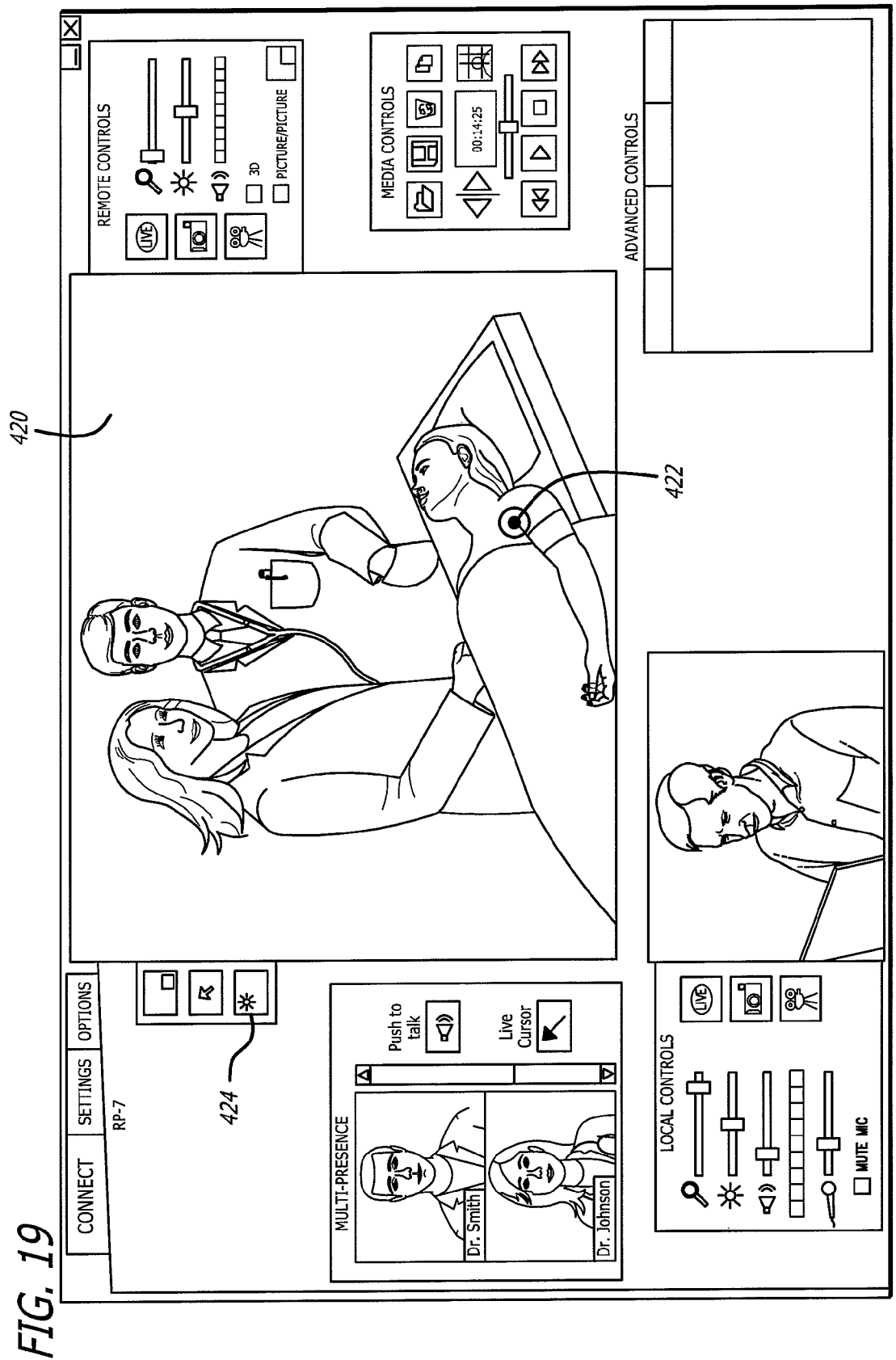
FIG. 19 is an illustration of a user interface for a robot with a laser pointer.

FIG. 19 is an embodiment of a DUI 420 that is connected to a non-mobile robot that includes a laser pointer such as the robot shown in FIGS. 4-8. Because the robot is not mobile the platform graphics are not shown (compare with field 402 in FIG. 17). Likewise, because the robot does not have a projector the projector field is not displayed (compared with FIG. 18). The DUI 420 includes a graphical cursor circle 422 and a graphical button 424 that can be used to activate and deactivate the laser pointer. Circle 422 and 424 are only displayed when the remote station accesses a robot with a laser pointer. Upon enabling the laser pointer, the cursor 422 disappears. User input, such as movement of a mouse, is translated by the system into movement of the laser pointer. The visual feedback to the user is the laser as recorded by the robot camera and transmitted to the remote station for display on the DUI 420.

The coordinate transforms that are used to transform user input commands to robot movement may be remapped to account for the difference in location between the laser pointer and the camera and the fact that the laser is projected into three dimensional space. The system may utilize the camera's focus length to remap the commands. Alternatively, optical recognition can be utilized to remap the commands to move the laser and/or robot head. A servo routine can be implemented to iteratively move the laser pointer so that the laser points to the same location as the graphical cursor on the screen.

The system may have a laser scroll feature where the robot head automatically moves wherein the laser is always within the field of view of the robot camera. The system can utilize optical recognition to determine whether the end of the laser is in the robot camera field of view. Additionally, the head can be moved automatically if the user attempts to command a movement of the laser that is outside the range of the actuator(s) that moves the laser pointer.

The laser can be used to start and/or operate another device. For example, an OR machine may have an optical input sensor panel. The user can direct the laser onto the panel to control the device. The system can be programmed so that the laser pointer is moved to continuously create a box or circle. The continuously created box or circle may indicate to a person at the robot site the remote station field of view (e.g., what the user sees). The laser pointer can be moved in a raster scan manner to project an image onto a surface such as a screen. For example, the image may be a picture or document. The laser pointer can be used to project information such as an image. The laser pointer can also be utilized to find a range of an object. For example, the laser can be scanned over a three dimension object. The resulting images captured by the robot camera can be analyzed and utilized to guide the robot to avoid obstacles.

The laser pointer can be utilized as an aid to assist users in various tele-presence applications. For example, the laser pointer can be used at a surgical site to point at an anatomical location where retraction, incision, sutures and/or trocars are to occur. The head can be moved back and forth to face the patient and a doctor. The movement of the laser pointer may be independent of the head movement. Although a laser pointer is described the system may include a medical or industrial laser that can perform operations such as cutting and/or ablating.

The system may also provide graphical buttons that allow a user to select between a normal cursor mode, a live cursor mode and a laser pointer mode. In the normal cursor mode the user can zoom, telestrate, etc. with the cursor. In the live cursor mode the user can point to portions of the robot image that is displayed to a guest and/or the robot monitor. In laser pointer mode the robot moves in conjunction with movement of the laser pointer.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for creating a display user interface for a robot system, comprising:

accessing, from a remote control station, one of a plurality of telepresence robots, the plurality of telepresence robots including a first robot that has a first capability and a second robot that does not have said first capability;

and, displaying the display user interface at the remote control station, the display user interface displays at least one field that corresponds to said first capability when the first robot is accessed and does not display said at least one field when the second robot is accessed, wherein the remote control station includes software with at least one object that relates to said first capability, the remote control station instantiates the at least one object when the first robot is accessed and does not instantiate the at least one object when the second robot is accessed.

2. The method of claim 1, wherein said first capability includes a mobile platform and said at least one field corresponds to a robot platform.

3. The method of claim 1, wherein said first capability includes a projector and the at least one field is a projector field.

4. The method of claim 1, wherein said first capability includes a laser pointer and the at least one field is a graphic corresponding to the laser pointer.

* * * * *